US006821117B2

(12) United States Patent
Burtscher et al.

(10) Patent No.: US 6,821,117 B2
(45) Date of Patent: Nov. 23, 2004

(54) LIGHT HARDENING APPARATUS FOR EFFECTING THE LIGHT HARDENING OF DENTAL RESTORATION PIECES

(75) Inventors: Peter Burtscher, Rankweil (AT); Wolfgang Plank, Rankweil (AT); Gottfried Rohner, Altstatten (CH)

(73) Assignee: Ivocler Vivadent AG, Schaan (LI)

( * ) Notice: Subject to any disclaimer, the term of this patent is extended or adjusted under 35 U.S.C. 154(b) by 116 days.

(21) Appl. No.: 10/139,308

(22) Filed: May 6, 2002

(65) Prior Publication Data

US 2002/0172918 A1 Nov. 21, 2002

Related U.S. Application Data

(60) Provisional application No. 60/307,073, filed on Jul. 20, 2001.

(30) Foreign Application Priority Data

May 23, 2001 (DE) .......................................... 101 25 343

(51) Int. Cl.[7] ................................................. A61C 3/00
(52) U.S. Cl. ......................................................... 433/29
(58) Field of Search ........................................... 433/29

(56) References Cited

U.S. PATENT DOCUMENTS

| 5,420,768 | A | 5/1995 | Kennedy | 362/119 |
|---|---|---|---|---|
| 5,634,711 | A | 6/1997 | Kennedy et al. | 362/119 |
| 6,331,111 | B1 | * 12/2001 | Cao | 433/29 |
| 6,638,063 | B2 | * 10/2003 | Otsuka | 433/29 |
| 2002/0080464 | A1 | * 6/2002 | Bruns | 359/290 |

FOREIGN PATENT DOCUMENTS

| DE | 295 11 927 U1 | 2/1997 |
|---|---|---|
| DE | 19850834 A1 | 5/2000 |

* cited by examiner

*Primary Examiner*—John J Wilson
(74) *Attorney, Agent, or Firm*—John C. Thompson; Alan S. Korman

(57) ABSTRACT

A light hardening apparatus for effecting the photopolymerization of a light hardenable dental restoration material is provided and includes a plurality of light sources supported on semi-conductor bases, which are mounted on a substrate. The light sources are arranged in at least two light source groups such that one group of light sources is disposed for irradiating a region of the dental restoration material and another group of light sources is arranged for irradiating a different region of the dental restoration material. The two groups of light sources are controllable to irradiate their respective associated regions of the dental restoration material independently of one another.

3 Claims, 2 Drawing Sheets

LIGHT HARDENING APPARATUS FOR EFFECTING THE LIGHT HARDENING OF DENTAL RESTORATION PIECES

CROSS-REFERENCE TO RELATED APPLICATIONS

This application claims foreign priority benefits under 35 U.S.C. §119 (a)–(d) from German patent application Ser. No. 101 25 343.5 filed May 23, 2001. In addition, this application claims the benefit under 35 U.S.C. §119 (e) of U.S. provisional patent application Ser. No. 60/307,073 filed Jul. 20, 2001.

BACKGROUND OF THE INVENTION

The present invention relates to a light hardening apparatus for effecting the light hardening of dental restoration pieces.

Light hardening apparatus for effecting light hardening within the dental field are currently configured either as a hand-held apparatus for the immediate light polymerization of a dental restoration piece in the mouth of a dental patient or as a stationary device.

Particularly in connection with hand-held devices, it is important that the polymerization be undertaken in a rapid manner especially if the limited time frame available for effecting a complete polymerization is to be respected as well in connection with larger dental fillings comprised of light-hardenable plastic or artificial material.

The conventional light hardening apparatus overwhelmingly comprise a halogen glow lamp having an integrated reflector whose light beam output is guided by a light guiding conduit having an outlet end disposed immediately proximate to the filling which is to be hardened. The usual light-hardenable dental plastic or artificial substances have a spectral sensitivity whose maximum lies in the range of visible light.

On the other hand, hand-maneuverable halogen glow lamps emit visible light with a substantially small UV portion of, for example, two percent. In order to improve the effectiveness of the light beam irradiation, it has been attempted to displace or shift the spectral sensitivity of the polymerizable plastic or artificial substance into the range of the long wavelength region. This, however, has only been successful to a limited extent.

It has further been proposed to shift the emitted spectral region to a higher frequency via a high wavelength light transmissive filter. However, in connection with this approach, a decidedly large amount of light beam energy must initially be produced so that the efficiency of the device is correspondingly poor. Typically, a cooling device must be deployed in order to limit the temperature of the light-hardening device which, however, results in an uncomfortable air stream for the dentist and/or the patient.

It is further known to deploy light hardening apparatus which work with semi-conductor light beam sources such as LEDs. For example, DE-GM 295 11 927 discloses a light-hardening device which uses a light diode which emits light in the blue spectral region and which is supplied from a battery or an accumulator.

It has, additionally, already been proposed to deploy a plurality of LEDs for the energy supply of the light guiding conduit. In this manner, the light output of the light-hardening device is improved. Independent of whether the LEDs are configured as module—that is, in a common plastic housing—or as individual LEDs—that is, each respectively disposed in an individual plastic housing—the light output of such arrangements is limited. The plastic surroundings do not effect an electrical insulation of the LEDs but, instead, block the transfer or giving off of heat by the LEDs, so that it is necessary, even with a cooling of the plastic housing from the exterior, that a predetermined density of the light emitting chips not be exceeded.

There have been numerous attempts to improve the light density of the conventional light hardening apparatus, in order to achieve a complete hardening of, as well, the deeper lying layers in a rapid manner. Heretofore, conventional light hardening apparatus having a lighting strength of, for example, 50 mW/cm$^2$ are able, in fact, to effect a correspondingly longer light irradiation of the plastic material to be polymerized so as to thereby produce a good hardening of the over surface. Deeper lying layers are, however, not at all hardened or, at most, are only incompletely hardened. There exists a hardness gradient which leads to the result that deeper lying regions remain soft or are only completely hardened after the complete hardening of the over surface regions.

The known light hardening apparatus lead to restoration results that are compromised by, or suffer from, in part, edge spalling problems. The known light hardenable plastic or artificial materials shrink or contract slightly during the hardening process. In connection with the known light hardening apparatus, a complete hardening initially is completed in the over/outer regions of the restoration piece. The thereafter following complete hardening of the deeper lying regions leads to contractions and, thus, to edge spalling formation.

Edge spalling problems occur in particular in connection with energy rich light hardening apparatus. On the other hand, a high energy density is desired with a correspondingly rapid complete hardening in order to make possible a rapid handling of the dental restoration piece that, as well, reduces the discomfort for the patient and leads to an improved work output in connection with the practice of a dentist.

SUMMARY OF THE INVENTION

The present invention offers a solution to the challenge of providing a light hardening apparatus for dental practice which reduces the tendency of light-hardenable masses to incur edge-spalling formation while at the same time permitting fabrication of such light hardening apparatus in a cost favorable manner and offering a light hardening apparatus which is flexible in its deployment.

In accordance with one embodiment of the light hardening apparatus of the present invention, it is particularly advantageous that the lighting intensity and, thus, the degree of complete hardening, can be accommodated to the requirements of the task by separate controls for the light sources for the various regions of the dental materials. In the edge region, for example, the dental restoration piece is typically thinner than in its middle region and, in the deployment of conventional light-hardening apparatus, the edge region is frequently thoroughly intensively hardened while the middle region with its larger layer thickness is only subjected to a hardening which meets the minimal interconnectivity requirements.

On the other hand, investigations have shown that a further hardening of an already completed hardened light and/or heat polymerizable plastic or other artificial material is not possible and, frequently, poor material properties must be accepted. In accordance with the current invention, these deficiencies are compensated for in that the separate control of the light sources for the various regions of the light-hardenable dental material can be accommodated to the requirements of the task. It is particularly advantageous in this connection that, in this manner, the possibility is offered to avoid the formation of edge spalling: edge spalling occurs through the contraction of the deployed plastic or artificial material during photo polymerization. With the light hardening apparatus of the present invention, the formation of edge spalls is prevented in that the separate control of the light sources for the various regions of the dental material is beneficially exploited such that, initially, a corresponding light source hardens one region and, thereafter, another region is hardened.

It is preferred that the one region is the middle portion, and the other region is the edge portion. In this configuration, the middle region is initially hardened by the first light source while the edge region is still soft, so that no edge spalls can occur.

In this connection, advantage is taken of the fact that during the complete hardening of a region, the contractions occurring thereat do not lead to the formation of edge spalls. At such a time point, the edge region of the plastic or artificial material is still fluid or is semi-fluid so that, during the complete hardening, no edge spalls occur.

The edge region includes, for example, a substantially reduced mass and, especially, a reduced width. The contraction in length in a transverse direction is in this connection clearly less by, for example, an order of magnitude of ten, so that the contractions remain within the expansion properties of the material. In this connection, the heretofore conventional light-hardening apparatus regularly completely hardened the edge regions due to the thereat reduced layer density. The edge regions in such circumstances not only had to compensate for their own contractions but, as well, had to compensate for the contractions in the considerably more voluminous middle regions, in order to avoid the formation of edge spalls, and this had to be accomplished although the edge regions also experienced a further hardening process conducted to ensure the complete hardening of the middle regions, whereupon the tendency of the edge regions to incur further diminution of their elasticity was detrimentally reinforced.

In accordance with the present inventions, the sequence of complete hardening is exactly reversed, which leads to the desired freedom from the formation of edge spalls.

It is possible to combine various LED-chips into groups for the light sources with one another in order to achieve a desired effect. The groups of chips can, in connection with this embodiment, also be individually controlled. For example, a group of targeted red light emitting chips can be deployed, if the light hardening apparatus is to perform a heat treatment. Through the individual control of the groups of chips, it is possible to also achieve a program controlled lighting effect if, for example, the light hardening is to be performed with light of different intensities. The diodes may be comprised of a selected one of a white color and another color. Furthermore, the groups of light diodes may be independently actuable, and those light diodes having substantially the same identity maximum are commonly actuable.

In accordance with a particularly advantageous embodiment of the light hardening apparatus of the present invention, it is provided that green emitting LED-chips are initially actuated to perform a pre-hardening, then an overflow of the material to be polymerized is removed, and thereafter a complete hardening at a wavelength of 420 nanometers is conducted.

It is particularly advantageous if the LED-chips are arranged in their plural arrangement in immediate adjacent neighboring relationships to the mass which is to be completely hardened, in order to perform the hardening process. In connection with this approach, there is offered for the first time the possibility to irradiate a selected region of the dental restoration piece with a selected LED light source. This approach permits, for example, the irradiation initially of the middle and typically deeper regions of the dental restoration piece to be conducted in an intensive manner. The hardening then follows so that, in effect, the central region is completely hardened. A contraction at this location is, however, not critical in connection with the formation of edge spalls, in that at this time point the edge regions have not been completely hardened. This represents a particularly advantageous advancement in the state of the art with respect to the heretofore conventional uniform hardening, whereby the formation of edge spalls is drastically reduced or even completely avoided.

Further details, advantages, and features are described in the hereinafter following description of several embodiments of the light apparatus of the present invention when taken in conjunction with the figures of the drawings.

The object and advantages of the present invention will appear more clearly from the following specification in conjunction with the accompanying schematic drawings, in which:

DETAILED DESCRIPTION OF THE PREFERRED EMBODIMENTS

Figure 1:
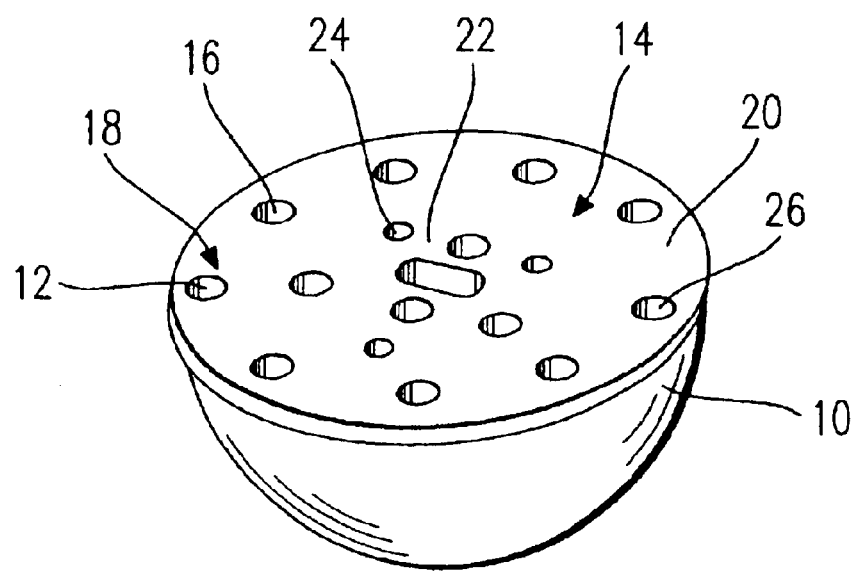
FIG. 1 is a perspective view of details of one embodiment of the light hardening apparatus of the present invention showing, in particular, a base body having integrated light sources.

As seen in FIG. 1, the light hardening device in accordance with the present invention includes a base body 10 on which are mounted a plurality of LED-chips 12 on the upper side 14 of the base body. The LED-chips 12 are each respectively secured in hollows or recesses 16 and are in sunken disposition relative to the surface 18. A reflection region extends, as viewed from the LED-chips, toward the front at an angle. In the illustrated embodiment, seventeen of the chips 12 are provided, which are distributed over the upper side 14 of the base body 10 such that they form groups of the light sources.

The LED-chips 12 are so arranged that a portion thereof are disposed in the edge region 20 of the base body 10 and a further portion thereof are disposed in the middle region 22 of the base body 10. The chips 12 in the middle region 22 form the first light sources 24 and the chips in the edge region form the second light sources 26. The chips in the middle region 22 are substantially more performance robust than the chips in the edge region 20.

Figure 2:
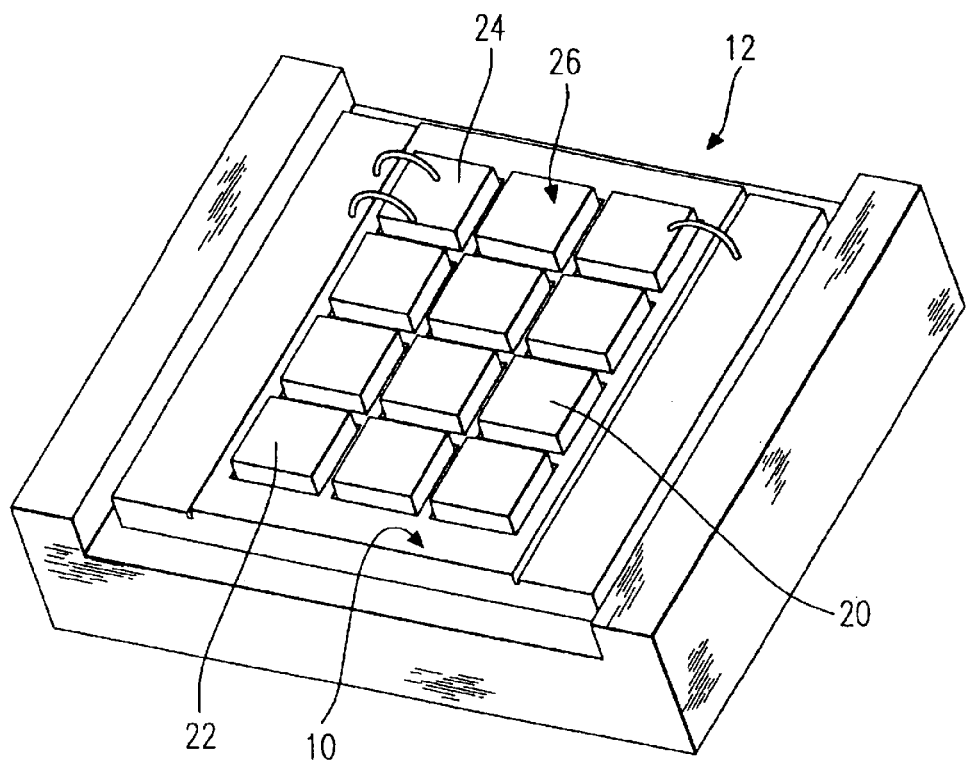
FIG. 2 is a perspective view of another embodiment of the light hardening apparatus of the present invention.

FIG. 2, another embodiment of the light hardening apparatus of the present invention can be seen. In this embodiment, the chips 12 are mounted in closer relationship to one another, whereby an edge region 20 with the first light sources 24 and a middle region 22 with the second light sources 26 are also formed. The LED-chips may have dimensions of approximately 1 mm×1 mm and may be disposable proximate to the dental restoration material for effecting the light hardening thereof.

Figure 3:
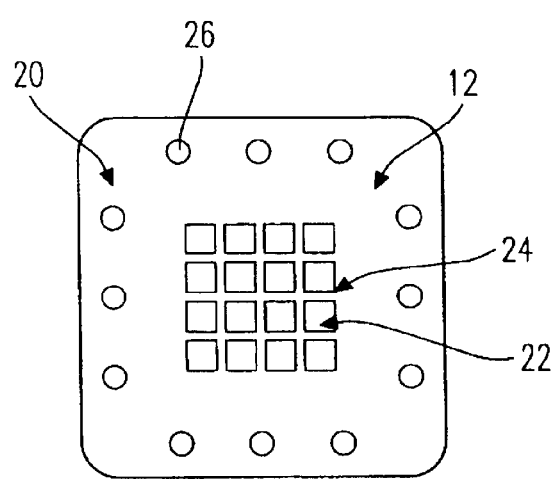
FIG. 3 is a top plan view of a further embodiment of the light hardening apparatus of the present invention.

A further embodiment of the light hardening apparatus of the present invention is shown in FIG. 3. In this embodiment, a total of sixteen of the chips 12 are provided to form the first light sources 24 in the middle region 22, while a total of twelve of the chips 12 are provided to form the second light sources 26 in the edge region 20.

Under the control of the control device of the present invention, the first light sources 24 are initially actuated when the light hardening apparatus is disposed in immediate proximate relationship with the surface of a dental restoration piece which is to be hardened. Following the complete hardening of the middle regions, the second light sources 26 are actuated in order to effect the complete hardening of the edge region of the dental restoration piece.

It is to be understood that any suitable desired partitioning or distribution of the light sources can be undertaken within the scope of the invention. Thus, LEDs of higher light performance can be densely arranged in the middle region 22 while, in the edge region 20, the light sources can comprise those having a reduced performance and can be arranged at a lower density.

The light sources can be comprised of LEDs or LED-arrays which emit light of various wavelengths and which can be maintained separate or combined together. In this connection, the surface to be irradiated can be irradiated in a controlled manner and one achieves thereby a controlled polymerization of the photo polymerizable dental material (from left to right, in a carpet manner from outside to inside, from inside to outside, etc.). This controlled surface irradiation can be still further optimized if one can deploy at least two different photo catalyzer materials for the dental material, each of which possesses a different intensity maximum. Through the time shifted control of the light sources, a first portion of the dental material can be initially hardened and, thereafter, a further portion of the dental material can be hardened.

In accordance with the present invention, it is particularly advantageous that the light hardening apparatus can directly irradiate the dental restoration piece without the need to intermediately guide the irradiation location via a light guiding element. The apparatus is preferably mounted at the head of a dental practice instrument and is operable to effect the light polymerization of a light polymerizable dental restoration piece. The two light source groups may be disposed in an annular relationship to one another such that they irradiate a dental restoration piece which is to be hardened from two differing angles.

The present invention is, of course, in no way restricted to the specific disclosure of the specification and drawings, but also encompasses any modifications within the scope of the appended claims.

What is claimed is:

1. A light hardening apparatus for effecting the photopolymerization of a light hardenable dental restoration material, comprising:

a plurality of light sources supported on a base, the light sources being arranged in at least two light source groups such that one group of light sources is disposed for irradiating an associated first region of the dental restoration material and another group of light sources is arranged for irradiating an associated second region of the dental restoration material, wherein the two light source groups are disposed in an angular relationship to one another such that they irradiate a dental restoration piece which is to be hardened from two differing angles; and means for controlling the two groups of light sources to cause them to irradiate their respective associated regions of the dental restoration material independently or one another.

2. A light hardening method for effecting the photopolymerization of a light hardenable dental restoration material, comprising:

providing a base;

providing a plurality of light sources supported on the base, the light sources being arranged in at least two light source groups such that one group of light sources is disposed for irradiating an associated first region of the dental restoration material and another group of light sources is arranged for irradiating an associated second region of the dental restoration material; and controlling the two groups of light sources to cause them to irradiate their respective associated regions of the dental restoration material independently of one another.

3. A light hardening apparatus for effecting the photopolymerization of a light hardenable dental restoration material, comprising:

a base;

a plurality of light sources supported on a base, the light sources being arranged in at least two light source groups such that one group of light sources is disposed for irradiating an associated first region of the dental restoration material and another group of light sources is arranged for irradiating an associated second region of the dental restoration material, each of the light sources being a group of LEDs, the first group emitting either white light or a colored light such as red, blue or green, and the second group of LEDs emitting light of a differing color;

means for controlling the two groups of light sources to cause them to irradiate their respective associated regions of the dental restoration material independently of one another, wherein the apparatus is operable to effect the light polymerization of a light polymerizable dental restoration piece, wherein the first group of LEDs is mounted centrally within the second group of LEDs, the first group of LEDs being controlled to initially harden a central region of a dental restoration, and the second group of LEDs subsequently hardening an edge portion whereby edge spall's are substantially minimized.

* * * * *